(12) United States Patent
    Haack et al.

(10) Patent No.: US 12,611,215 B2
(45) Date of Patent: Apr. 28, 2026

(54) ENDOSCOPIC CLIP

(71) Applicant: MICRO-TECH (NANJING) CO., LTD., Nanjing (CN)

(72) Inventors: Scott Haack, Chardon, OH (US); Hongyan Jin, Nanjing (CN); Xiaojun Ma, Nanjing (CN); Weiqin Qiu, Nanjing (CN)

(73) Assignee: MICRO-TECH (NANJING) CO., LTD., Nanjing (CN)

( * ) Notice: Subject to any disclaimer, the term of this patent is extended or adjusted under 35 U.S.C. 154(b) by 249 days.

(21) Appl. No.: 18/271,321

(22) PCT Filed: Jun. 10, 2022

(86) PCT No.: PCT/CN2022/098161
    § 371 (c)(1),
    (2) Date: Jul. 7, 2023

(87) PCT Pub. No.: WO2022/262656
    PCT Pub. Date: Dec. 22, 2022

(65) Prior Publication Data
    US 2024/0058014 A1    Feb. 22, 2024

Related U.S. Application Data

(60) Provisional application No. 63/210,068, filed on Jun. 13, 2021.

(51) Int. Cl.
    *A61B 17/122*    (2006.01)
    *A61B 17/128*    (2006.01)
(52) U.S. Cl.
    CPC ........ *A61B 17/122* (2013.01); *A61B 17/1285* (2013.01)

(58) Field of Classification Search
    CPC ..... A61B 17/08; A61B 17/083; A61B 17/122; A61B 17/1227; A61B 17/1285;
    (Continued)

(56) References Cited

U.S. PATENT DOCUMENTS

| 5,695,505 A | * | 12/1997 | Yoon | ...................... | A61B 17/12 |
| | | | | | 606/151 |
| 2002/0198549 A1 | * | 12/2002 | Sixto, Jr. | ................... | G01B 7/10 |
| | | | | | 606/157 |
| 2005/0250988 A1 | * | 11/2005 | Ewers | ................... | A61B 1/0014 |
| | | | | | 600/102 |

FOREIGN PATENT DOCUMENTS

| CN | 101588760 A | 11/2009 |
| CN | 101917935 A | 12/2010 |

(Continued)

*Primary Examiner* — Diane D Yabut
(74) *Attorney, Agent, or Firm* — Mandar A. Joshi; Bret E. Field; Bozicevic, Field & Francis LLP

(57) ABSTRACT

A clip (100) for use in an endoscopic gastrointestinal procedure includes a first arm (110), a second arm (120), and an end effector (130). The first arm (110) includes a first proximal end (110*b*) and a first distal end (110*a*). The second arm (120) includes a second proximal end (120*b*) and a second distal end (120*a*). The end effector (130) is fixedly coupled to the second arm (120) and extends from the second arm (120) distally relative to the second distal end (120*a*). The first arm (110) and the second arm (120) are pivotable relative to each other between an open position and a closed position in which tissue is clampable between the first arm (110) and the second arm (120). The end effector (130) is configured to be inserted into the tissue by rotating the clip (100) about a first axis (130*a*).

11 Claims, 10 Drawing Sheets

(58) Field of Classification Search
     CPC .......... A61B 17/0487; A61B 2017/081; A61B
                   2017/00818; A61B 2017/0649; A61B
                                            2017/00349
     See application file for complete search history.

(56)                  References Cited

FOREIGN PATENT DOCUMENTS

| CN | 102274061 A | 12/2011 |
|----|-------------|---------|
| CN | 103442658 A | 12/2013 |
| CN | 205019140 U | 2/2016 |
| CN | 110958861 A | 4/2020 |
| WO | WO0245603 A1 | 6/2002 |

* cited by examiner

ENDOSCOPIC CLIP

CROSS-REFERENCE TO RELATED APPLICATION(S)

This application claims the benefit of U.S. Provisional Application No. 63/210,068, filed Jun. 13, 2021, which is hereby incorporated by reference in its entirety for all purposes.

TECHNICAL FIELD

This disclosure relates to endoscopy and, in particular, clips for gastrointestinal endoscopy.

BACKGROUND

Hemostasis clips are used in endoscopic gastrointestinal procedures to prevent bleeding and provide closures to small defects in gastrointestinal tissue (e.g., to close incisions). Hemostatic clips generally include two arms that clamp together, so as to hold tissue therebetween. The arms typically include ends thereon that are bent toward each other and/or shaped (e.g., with serrations) to frictionally engage the gastrointestinal tissue to move the tissue between the arms prior to clamping the tissue therewith. However, by relying on friction to move the tissue with the arms, clinicians may have limited ability to move the tissue to provide closures to various defects in the tissue. Moreover, due to the size constraints of the endoscopic procedures, the hemostatic clips may be small in size relative to a defect in the tissue, thus requiring several hemostatic clips to provide closure thereto.

SUMMARY

Disclosed herein are implementations of clips for use in endoscopic gastrointestinal procedures.

In one implementation, a clip for use in an endoscopic gastrointestinal procedure generally includes a first arm, a second arm, and an end effector. The first arm includes a first proximal end and a first distal end. The second arm includes a second proximal end and a second distal end. The end effector is fixedly coupled to the second arm and extends from the second arm distally relative to the second distal end. The first arm and the second arm are pivotable relative to each other between an open position and a closed position in which tissue is clampable between the first arm and the second arm. The end effector is configured to be inserted into the tissue by rotating the clip about a first axis.

The first axis that may be generally perpendicular to a second axis about which one or more of the first arm and the second arm are pivotable between the open position and the closed position. The end effector may be configured to be inserted into the tissue by at least one rotation thereof about the first axis, such as by at least two rotations thereof about the first axis.

The end effector may include a helical portion having one or more turns that circumscribe the first axis. When in the closed position, at least one of the one or more turns distally beyond the first distal end of the first arm. The helical portion may include a distal end that is sharpened. The distal end of the helical portion may include a barb. The first arm may include a first mid-segment that extends between the first distal end and the first proximal end, the second arm may include a second mid-segment that extends between the second distal end and the second proximal end, and one or both of the first mid-segment and the second mid-segment may include teeth that engage and retain the tissue when clamped between the first arm and the second arm.

In one implementation, a clip for use in an endoscopic gastrointestinal procedure generally includes a housing, an arm pivotally coupled to the housing and having a proximal end and a distal end, and a helical portion coupled to and extending distally from the housing. In a closed configuration, the distal end is positioned adjacent to a proximal end of the helical portion and in an open configuration, the distal end is pivoted away from the helical portion.

The proximal end may define a cam surface that extends through the proximal end and defines a path, and a pin may be located in the path. The pin is movably coupled to the housing and interfaces with the cam surface to cause the arm to move between the closed configuration and the open configuration. The arm is also configured to move distally relative to the housing to position the distal end adjacent to a distal end of the helical portion.

In one implementation, a clip for use in an endoscopic gastrointestinal procedure generally includes a first arm, a second arm, and an end effector. The first arm includes a first proximal end and a first distal end. The second arm includes a second proximal end and a second distal end. The end effector is located between the first arm and the second arm and is movable in an axial direction relative to the first arm and the second arm and is configured to be inserted into tissue by rotating the end effector about a first axis. The first arm and the second arm are pivotable relative to each other between an open position and a closed position in which tissue is retained between the first arm and the second arm.

The end effector may be configured to rotate relative to the first arm and the second arm and may include a helical portion. The helical portion may include a distal end with a barb configured to retain the tissue. The first arm may include a first mid-segment with first serrations, and the second arm may include a second mid-segment with second serrations, and the first and second serrations may be configured to intermesh when the clip is in the closed position.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Disclosed herein are embodiments of clips to be used in endoscopic gastrointestinal procedures. The clip includes two arms that clamp tissue therebetween. In one implementation, one of the arms includes an end effector that is configured, prior to clamping the tissue, to pierce into and retain the tissue thereon to form a positive connection therewith. In another implementation, the end effector is positioned between the arms. More particularly, the end effector is configured to pierce and be inserted into the tissue through rotational motion, for example, being configured as a helix. The positive connection of the clip to the tissue may allow the clinician to manipulate (e.g., move) the tissue in different manners that might not be possible with frictional engagement, for example, by drawing the tissue across relatively large defects that and/or by drawing the tissue rearward toward the endoscope.

Figure 1:
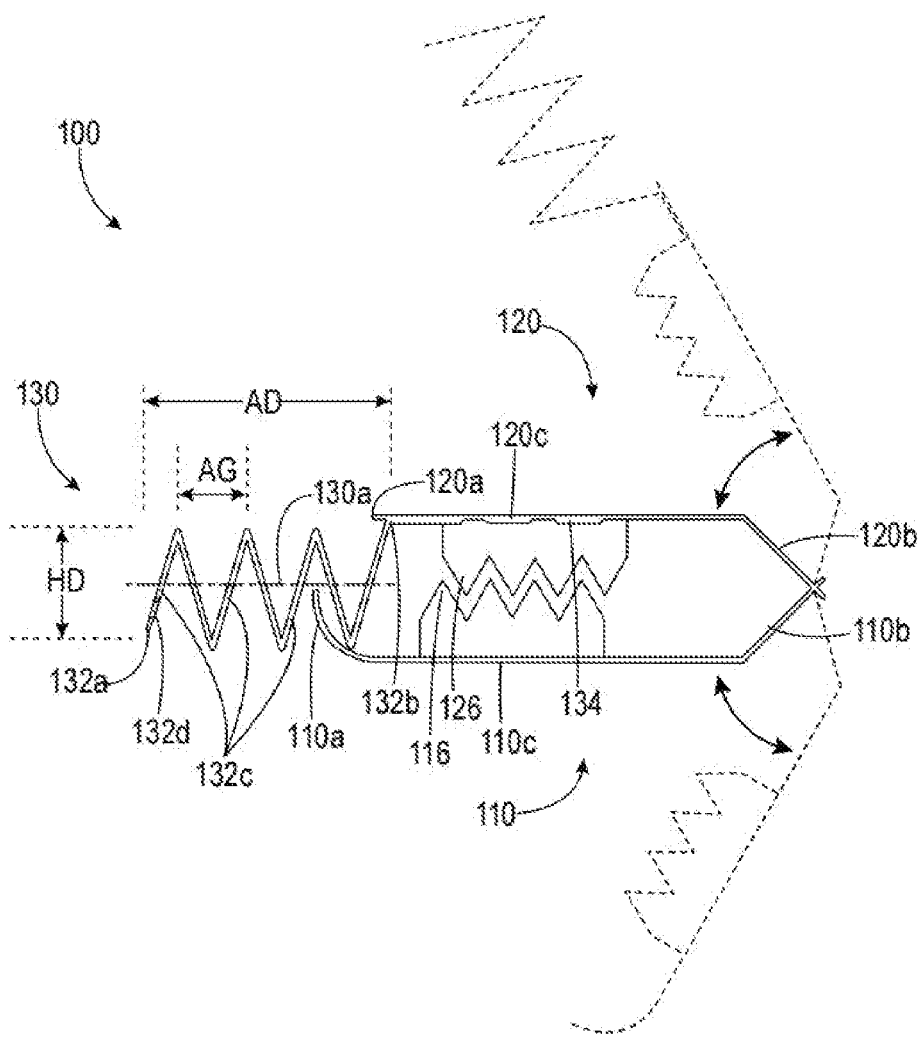
FIG. 1 is a side view of an embodiment of an endoscopic gastrointestinal clip depicted in a closed position (solid lines) and an open position (dashed lines).

Referring to FIG. 1, a clip 100 is configured to be used in endoscopic gastrointestinal procedures to provide closure to large defects in gastrointestinal tissue. The clip 100 generally includes a first arm 110, a second arm 120, and an end effector 130.

Figure 6A:
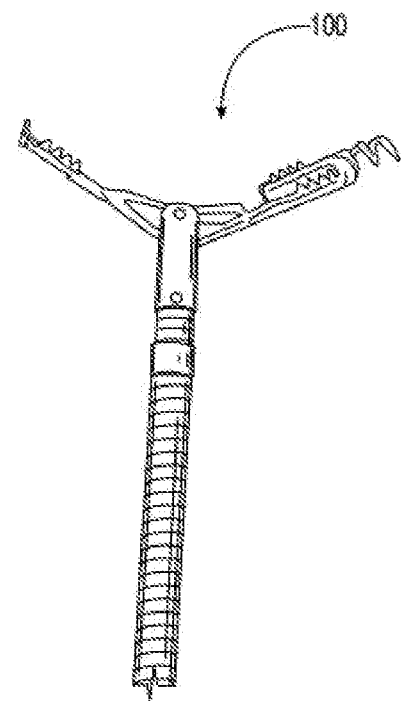
FIGS. 6A and 6B are perspective views an embodiment of the endoscopic gastrointestinal clip in the open and closed positions, respectively.
Figure 6B:
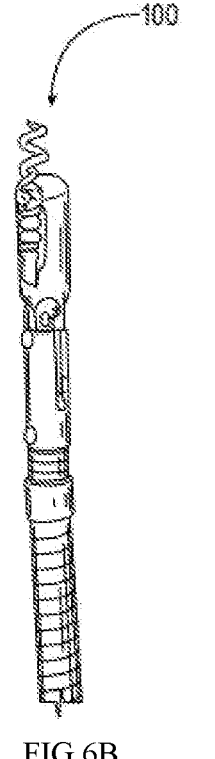

The first arm 110 and the second arm 120 are movable relative to each other between a closed position (illustrated in solid lines in FIG. 1) and an open position (illustrated in dashed lines in FIG. 1). The clip 100 is also shown in FIGS. 6A and 6B in the open and closed positions respectively. The first arm 110 is elongated and includes a first distal end 110a, a first proximal end 110b, and a first mid-segment 110c extending between the first distal end 110a and the first proximal end 110b. The second arm 120 is elongated and includes a second distal end 120a, a second proximal end 120b, and a second mid-segment 120c extending between the second distal end 120a and the second proximal end 120b. While the identifiers of "first" and "second" are used to distinguish between the first arm 110 and the second arm 120 and the features thereof (e.g., between the first distal end 110a of the first arm 110 and the second distal end 120a of the second arm 120), such terms may be referred to cooperatively (e.g., the arms 110, 120) or other identifiers may be used (e.g., an arm 110 and another arm 120).

The clip 100 is configured to open and close to receive and clamp the tissue therein. The clip 100 is initially closed when inserted through an endoscope and into a patient, is subsequently opened to receive the tissue therein, and is then permanently closed to clamp and retain the tissue therein. Before being permanently closed, the clip 100 may be opened and closed repeatedly, for example, when manipulating the tissue.

To open and close the clip 100, the two arms 110, 120 are pivotable about the proximal ends 110b, 120b, respectively, thereof between open and closed positions. The two arms

110, 120 may be pivotable in any suitable manner, for example, being pivotable about a single fixed pivot axis extending through the proximal ends 110b, 120b thereof as is illustrated in FIG. 1 (e.g., with a hinge pin), two fixed pivot axes that are each associated with one of the two proximal ends 110b, 120b, with a moving pivot axis (e.g., formed by a sliding interface or linkage directly or indirectly between the proximal ends 110b, 120b of the two arms 110, 120), or any other suitable manner by which the an angle between the two arms 110, 120 is reduced to bias the two arms 110, 120 toward each other. In one non-limiting example, the two arms 110, 120 may be pivotable and fixable (e.g., lockable in the closed position) relative to each other as described in U.S. Pat. No. 9,795,390, the entire disclosure of which is incorporated by reference herein.

When the clip 100 is closed, the two arms 110, 120 are biased toward each other, such that the distal ends 110a, 120a, respectively, thereof are in close proximity with each other. When the clip 100 is open, the two arms 110, 120 are biased away from each other, such that the distal ends 110a, 120a, respectively, thereof are spaced apart to form an opening therebetween. An angle between the two arms 110, 120 may change, for example, between 0 and 180 degrees (e.g., between 115 and 155 degrees) when moved between the open and closed positions. As illustrated in dashed lines in FIG. 1, the two arms 110, 120 are pivoted apart by 120 degrees. Depending on the configuration of the arms 110, 120, the distal ends 110a, 120a, the mid-segments 110c, 120c, and the end effector 130, the first distal end 110a of the first arm 110 may be in contact with the second distal end 120a of the second arm 120 or the end effector 130 when the clip 100 is closed (e.g., when being inserted through the endoscope and/or after clamping the tissue therein).

Each of the two arms 110, 120 may be formed of a biocompatible metal material according to any suitable combination of metal shaping operations. For example, the two arms 110, 120 may be formed of surgical stainless steel, such as SAE 316L, cobalt chromium, or nitinol. The two arms 110, 120 may be formed by stamping operations (e.g., to form an overall shape of the arms 110, 120) and/or grinding operations (e.g., to form apertures and other features of the two arms 110, 120, such as serrations). Each of the two arms 110, 120 may be formed as a unitary component (e.g., with monolithic material) or may be form of multiple components that are coupled (e.g., welded, glued, or otherwise bonded) to each other.

Various configurations and features of the arms 110, 120 are discussed in further detail below.

Figure 7:
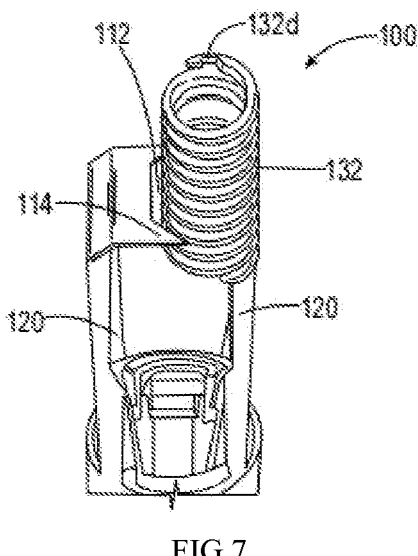
FIG. 7 is a perspective view of an embodiment of the endoscopic gastrointestinal clip.

The end effector 130 is fixedly coupled to the second arm 120 and extends distally past the distal end 120a thereof. As referenced above, the end effector 130 is configured to pierce into and retain therein the tissue of the patient. More particularly, the end effector 130 is configured to pierce and be inserted into the tissue through rotational motion generally about a longitudinal axis of the endoscope, which may be generally perpendicular to a pivot axis about which the two arms 110, 120 are moved between the open and closed positions). As shown and described below, in one embodiment, the end effector 130 includes a helical portion 132 and a coupling portion 134. The helical portion 132 is shaped as a helix and includes a distal end 132a, a proximal end 132b, and one or more turns 132c extending therebetween (e.g., four of the turns 132c, as shown). The distal end 132a is configured to pierce the tissue and may be sharpened or otherwise pointed. The distal end 132a may further include a barb 132d to facilitate retention of the tissue on the distal end 132a, for example, as the distal end 132a first pierces the tissue (see also FIG. 7). Though the helical portion 132 is described as being shaped as a helix, additional shapes and/or configurations may be used to pierce and retain tissue as further described herein. For example, the helical portion 132 may also include different shapes and/or configurations such as a bayonet configuration, a barbed configuration, a stepped configuration, etc.

The coupling portion 134 extends proximally from the proximal end 132b and is fixedly coupled to the second arm 120, for example, being welded or otherwise bonded to and extending along an interior surface of the mid-segment 120c. The coupling portion 134 may, for example, extend substantially straight. Alternatively, the proximal end 132b of the helical portion may be coupled directly to the second distal end 120a of the second arm 120.

The end effector 130 is formed of a biocompatible metal according to any suitable combination of manufacturing processes. For example, the end effector 130 may be formed of the same material as the second arm 120 or any other suitable metal, such as surgical stainless steel. The end effector 130 may be formed via extrusion (e.g., to form a wire) and bending operations.

Further aspects of the end effector 130 are discussed in further detail below.

Still referring to FIG. 1, the helical portion 132 of the end effector 130 may be configured according to various characteristics to facilitate piercing and retention of the tissue thereon, such characteristics including axial distance AD and/or number of turns 132c, helical dimension HD, wire dimension (not labeled), and/or pitch or axial gap AG between turns.

The axial distance AD refers to the distance that the helix extends along an axis 130a thereof, which may be measured relative to the first distal end of the first arm 110 and/or the second distal end of the second arm 120. The axial distance AD may determine the amount (e.g., depth) of tissue that may be retained on the end effector 130. With more tissue being retained on the end effector 130, more force may be applied by the end effector 130 to the tissue for manipulation thereof (e.g., to draw the tissue across a large defect).

The axial distance AD may be defined as a linear distance (e.g., inches or mm) or by number of turns 132c. Each turn 132c of the helical portion 132 extends around (e.g., circumscribes) an axis 130a of the helical portion by 360 degrees. A partial one of the turns 132c extends around the axis 130a by less than 360 degrees. The helical portion 132 may, for example, include between one and eight turns (e.g., between three and six turns). The axial distance AD of the helical portion 132 may, for example, be between 1 mm and 15 mm. The end effector 130 and/or the helical portion 132 thereof may also be referred to as a helical needle.

One or more of the turns 132c are positioned distally of the distal end 110a of the first arm 110 (e.g., two, three, four, or more) when the clip 100 is closed. That portion of the axial distance AD extending distally beyond the first arm 110 may, for example, be between 1 mm and 10 mm), such as between 2 mm and 6 mm). As a result, when the clip 100 is closed, the helical portion 132 of the end effector 130 extends from the second arm 120 distally beyond the first arm 110 to engage and/or pierce the tissue (e.g., prior to the distal end 110a of the first arm 110 engaging the tissue). With the clip 100 remaining closed, the clip 100 is rotated generally about the axis 130a thereof such that the helical portion 132 is inserted into the tissue to be retained thereon. For example, the helical portion 132 may be inserted into the tissue via the rotational motion until substantially all of the turns 132c are inserted into the tissue and/or substantially all of the turns 132c distal of the distal end 110a of the first arm 110 are inserted into the tissue.

Figure 3:
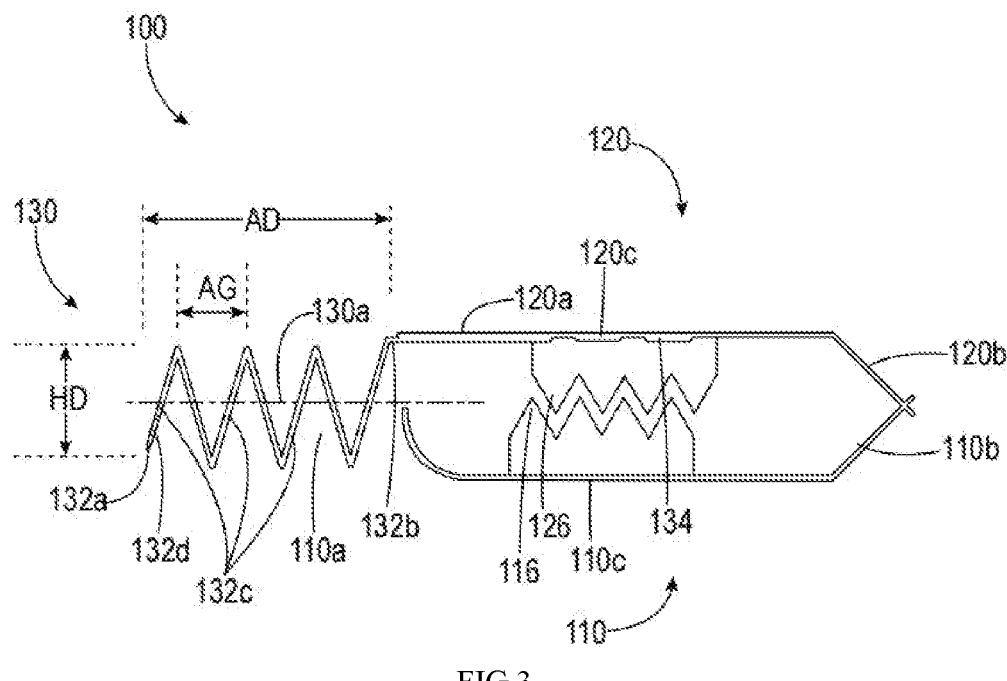
FIG. 3 is a side view of a second embodiment that is a variation of the endoscope gastrointestinal clip of FIG. 1.

When the clip 100 is closed, as shown in FIG. 1, the first arm 110 may axially overlap the helical portion 132 of the end effector 130 when the clip 100 is closed, for example, with the first distal end 110a terminating distally of at least a portion of one of the turns 132c (e.g., one of the turns 132c as shown). For example, when the clip 100 is closed, fewer than three of the turns 132c are positioned proximally of the distal end 110a of the first arm 110 (e.g., two, one, three-fourths, one half, or fewer of the turns 132c). Alternatively, as shown in FIG. 3, the turns 132c may be positioned entirely distally of the first arm 110 (e.g., none of the turns 132c are positioned proximally of the distal end 110a of the first arm 110).

The helical dimension HD refers to the outermost dimension (e.g., diameter) of the end effector 130 extending radially (i.e., perpendicular to the axis 130a of the helical portion 132). Similar to the axial distance AD of the helical portion 132, the helical dimension HD may determine the amount (e.g., width) of tissue that may be retained on the end effector 130. With more tissue being retained on the end effector 130, more force may be applied by the end effector 130 to the tissue for manipulation thereof (e.g., to draw the tissue across a large defect).

As shown, the helical dimension HD may be substantially constant over the axial distance AD of the helical portion 132 of the end effector 130. The helical dimension HD may be equal to or less than an outer dimension of the clip 100 measured between outer surfaces of the two arms 110, 120 when closed and substantially perpendicular to the axis 130a. For example, the helical dimension HD may be constant and between 1 mm and 3.2 mm, such as less than 3.2 mm or less than 2.8 mm (e.g., between 1.5 mm and 2.5 mm). Instead of being constant, the helical dimension HD may be variable, for example, increasing or decreasing as the helical portion 132 extends distally away from the distal end 120a of the second arm 120.

The wire dimension refers to the maximum cross-sectional dimension (e.g., diameter) of the wire forming the end effector 130. The wire dimensions impacts the ability of the helical portion 132 to be inserted into the tissue, with smaller diameters having less frictional engagement with the tissue to facilitate insertion. The wire dimensions additionally impact force transfer of the helical portion 132 to the tissue for manipulation thereof, with larger dimensions increasing the surface area over which force is transferred from the helical portion 132 to the tissue thereby preserving tissue integrity (e.g., limiting cutting thereof). The wire dimension may, for example, be a diameter of between 0.1 mm and 1.0 mm (e.g., 0.3 mm and 0.7 mm, such as 0.4 mm and 0.5 mm). The wire dimension may also be referred to as the wire diameter.

The axial gap AG refers to the distance measured parallel with the axis 130a between the wire of adjacent ones of the turns 132c. The axial gap AG may influence the amount of force that may be applied by the helical portion 132 to the tissue, with larger dimensions increasing the amount of tissue that is received between the turns 132c to preserve tissue integrity (e.g., limiting tearing thereof). The axial gap AG may be the result of the pitch and the wire dimension. The axial gap AG may be defined as a linear distance (e.g., inches or mm) or may be defined relative to other dimensions, such as a ratio of the wire dimension and/or helical diameter HD. The axial gap AG may, for example, be between one and four times the wire dimension. Instead or additionally, the axial gap AG may be between one and three times the helical dimension HD. The axial gap AG may, for example, be between 0.25 mm and 2.5 mm (e.g., between 0.5 mm and 2 mm, such as between 0.75 mm and 1.5 mm).

Figure 2:
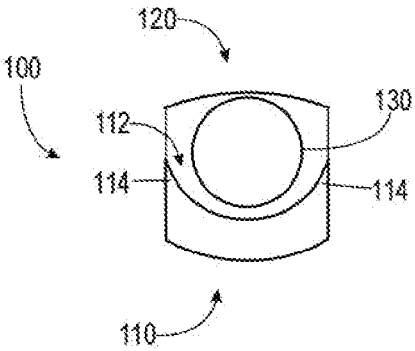
FIG. 2 is an end view of the endoscopic gastrointestinal clip of FIG. 1 depicted in a closed state.

Referring additionally to FIG. 2, one or more of the two arms 110, 120 may include further features to facilitate clamping and/or retention of the tissue in the clip 100. As shown in FIG. 1, the distal end 110*a* of the first arm 110 overlaps and is configured to receive therein the helical portion 132 of the end effector 130. For example, the distal end 110*a* defines a recess 112 in which is received a portion of the helical portion 132 when the clip 100 is closed (see also FIG. 7). The recess 112 may be defined between two teeth 114 of the distal end 110*a* that are intended to pierce or otherwise grab the tissue by localizing force applied thereto, so as to retain the tissue between the distal end 110*a* of the first arm and the helical portion 132 of the end effector 130 extending from the second arm 120.

Referring again to FIG. 1, one or more of the two arms 110, 120 may include teeth 116, 126 or other serrations along the mid-segments 110*c*, 120*c*, thereof. The teeth 116, 126 are intended to pierce or otherwise grab the tissue by localizing force applied thereto, so as to retain the tissue between the mid-segments 110*c*, 120*c* of the two arms 110, 120. The teeth 116, 126, when provided on both of the two arms 110, 120 may be configured to intermesh when the clip 100 is closed. The teeth 116, 126 extend generally toward the other of the arms 110, 120, for example, with the mid-segments 110*c*, 120*c* being formed as a bent (e.g., curved) structure having outer edges that extend generally toward the other of the arms 110, 120 and with the teeth 116, 126, respectively, being formed therein. The bent structure of the mid-segment 110*c*, 120*c* may also provide structural rigidity to the arms 110, 120, so as to apply force to the tissue to be clamped between the two arms 110, 120 in the clip 100.

Figure 4:
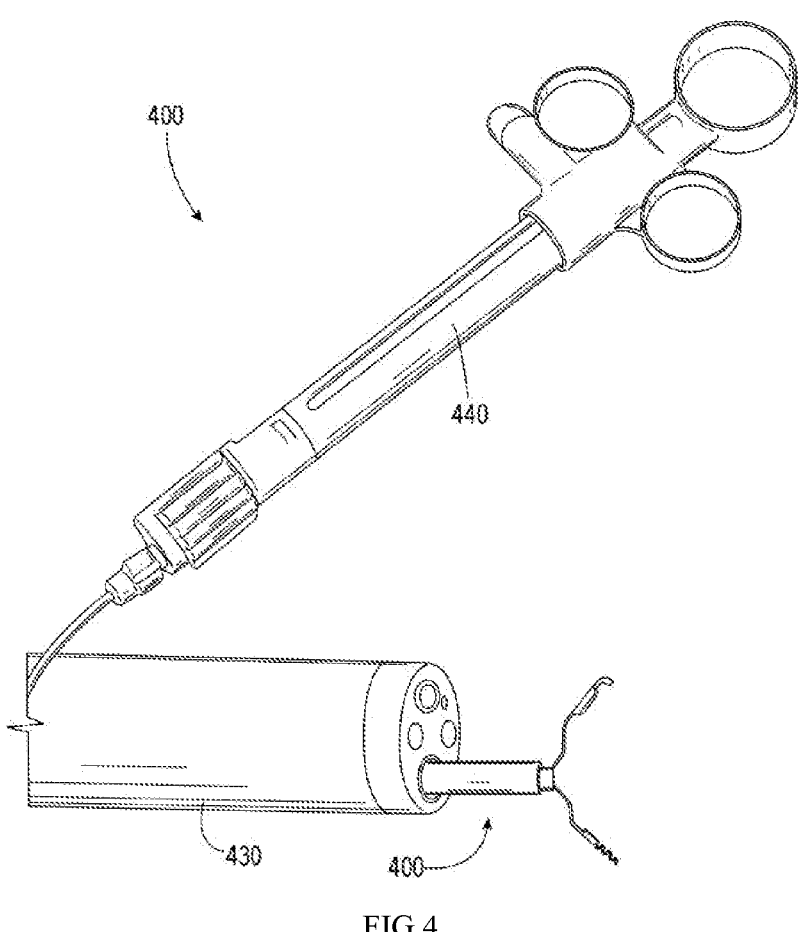
FIG. 4 illustrate an endoscopic system that includes an endoscopic gastrointestinal clip, an endoscope, a handheld control device, and an operational wire.

Referring to FIG. 4, an endoscopic system 400 includes the clip 100, an endoscope 430, a handheld control device 440, and an operational wire 450 extending through the endoscope 430 and operationally connecting the clip 100 and the handheld control device 440. The handheld control device 440, by manipulating the operational wire 450 (e.g., by pushing, pulling, and/or rotation) relative to the endoscope 430, may operate the clip 100 to rotate the clip 100 for insertion of the end effector 130 into the tissue, open and close the clip 100, and to lock the clip 100 in the closed position. For example, the clip 100 may be further configured to open, close, and fix into the closed position as described in U.S. Pat. No. 9,795,390, the entire disclosure of which is incorporated by reference herein.

Figure 5A:
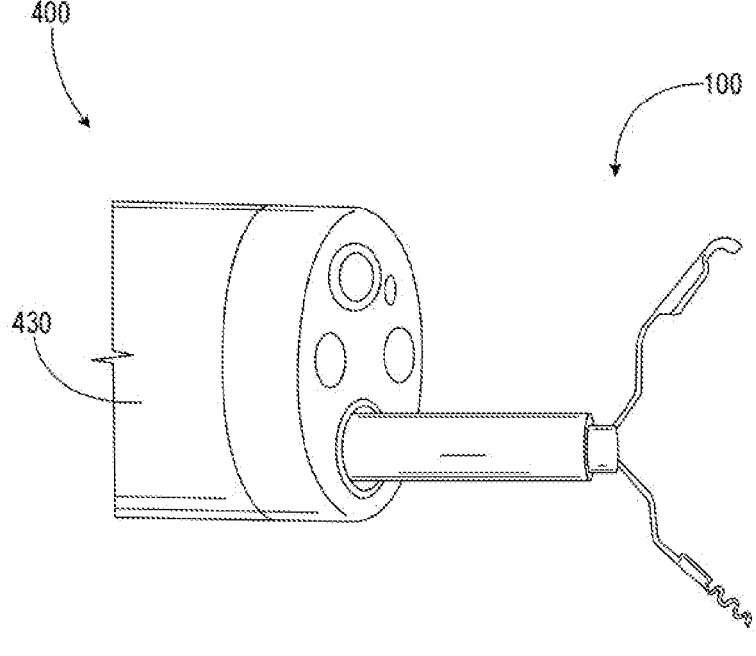
FIGS. 5A and 5B illustrate rotation and axial movement of the endoscopic gastrointestinal clip relative to an endoscope.
Figure 5B:
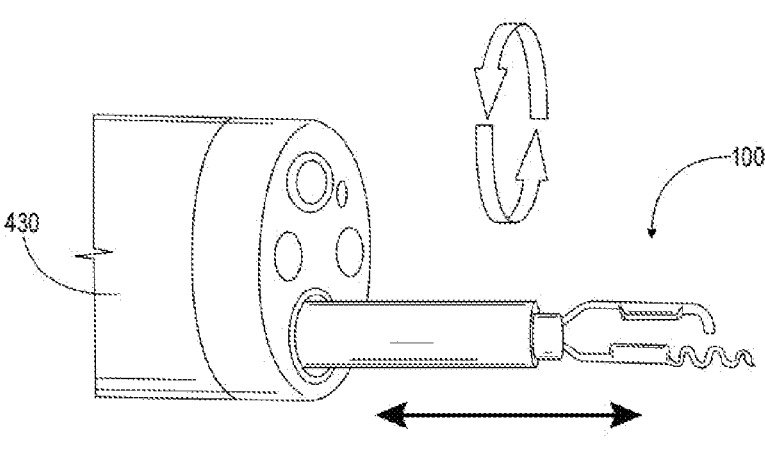

As is illustrated in FIGS. 5A and 5B, the clip 100 is extendable relative to the endoscope 430 and rotatable relative thereto for insertion of the clip 100 into the gastro-intestinal tissue.

Figure 8:
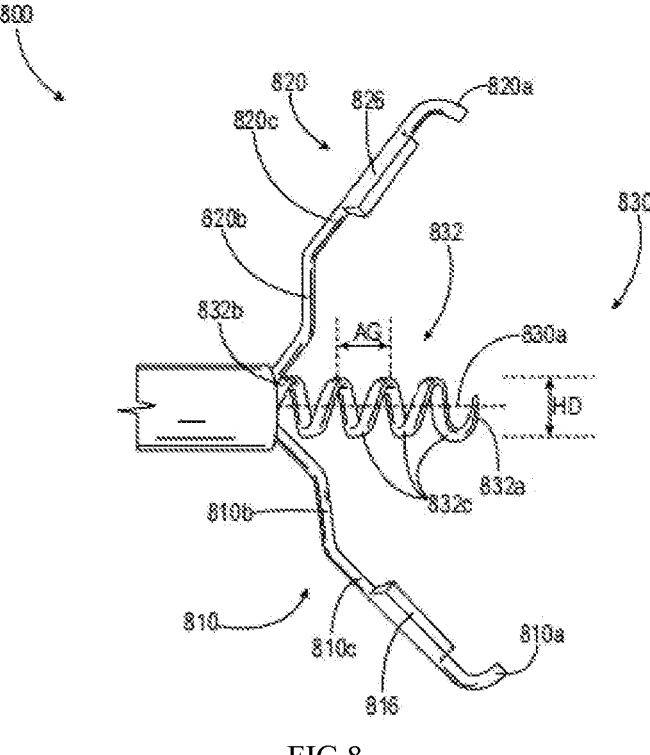
FIG. 8 is a side view of another embodiment of an endoscopic gastrointestinal clip in the open position.

Referring to FIG. 8, a side view of another embodiment of an endoscopic gastrointestinal clip 800 is shown in the open position. The clip 800 is configured to be used in endoscopic gastrointestinal procedures to provide closure to large defects in gastrointestinal tissue. The clip 800 generally includes a first arm 810, a second arm 820, and an end effector 830.

Figure 9A:
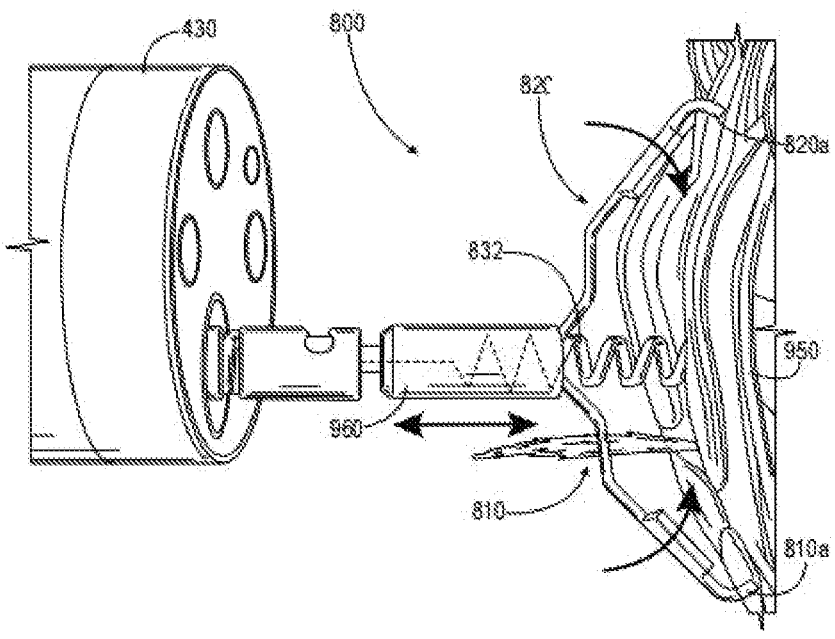
FIGS. 9A and 9B illustrate operation of the endoscopic gastrointestinal clip of FIG. 8 relative to an endoscope.
Figure 9B:
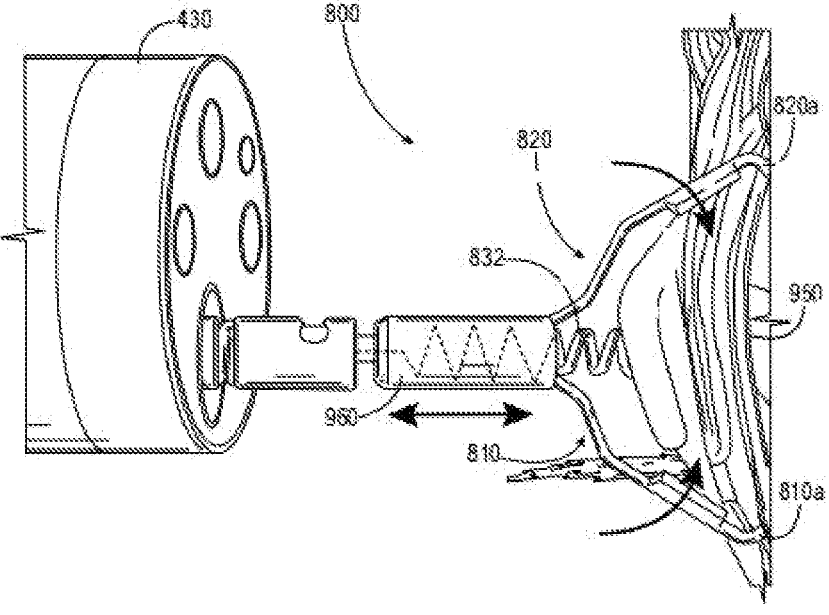

The first arm 810 and the second arm 820 are movable relative to each other between a closed position (a partially closed configuration is shown in FIG. 9B) and an open position shown in FIG. 8 and FIG. 9A. The first arm 810 and the second arm 820 are also movable independently of each other. For example, the first arm 810 may be configured to move regardless of the motion (or lack thereof) of the second arm 820. In addition, the second arm may be configured to move regardless of the motion (or lack thereof) of the first arm 810. Accordingly, in some implementations the first arm 810 may move toward the end effector 830 while the second arm 820 remains stationary. The second arm 820 may also move toward the end effector 830 while the first arm 810 remains stationary. Furthermore, the first arm 810 and the second arm 820 may be operated to move toward or away from the end effector 830 at different speeds. The first arm 810 is elongated and includes a first distal end 810*a*, a first proximal end 810*b*, and a first mid-segment 810*c* extending between the first distal end 810*a* and the first proximal end 810*b*. The second arm 820 is elongated and includes a second distal end 820*a*, a second proximal end 820*b*, and a second mid-segment 820*c* extending between the second distal end 820*a* and the second proximal end 820*b*. While the identifiers of "first" and "second" are used to distinguish between the first arm 810 and the second arm 820 and the features thereof (e.g., between the first distal end 810*a* of the first arm 810 and the second distal end 820*a* of the second arm 820), such terms may be referred to cooperatively (e.g., the arms 810, 820) or other identifiers may be used (e.g., an arm 810 and another arm 820).

The clip 800 is configured to open and close to receive and clamp (e.g., hold and/or retain) the tissue therein. The clip 800 is initially closed when inserted through an endoscope and into a patient, is subsequently opened to receive the tissue therein, and is then permanently closed to clamp and retain the tissue therein. Before being permanently closed, the clip 800 may be opened and closed repeatedly, for example, when manipulating the tissue.

To open and close the clip 800, the two arms 810, 820 are pivotable about the proximal ends 810*b*, 820*b*, respectively, thereof between open and closed positions. The two arms 110, 120 may be pivotable in any suitable manner, for example, being pivotable about a single fixed pivot axis extending through the proximal ends 810*b*, 820*b* thereof, two fixed pivot axes that are each associated with one of the two proximal ends 810*b*, 820*b*, with a moving pivot axis (e.g., formed by a sliding interface or linkage directly or indirectly between the proximal ends 810*b*, 820*b* of the two arms 810, 820), or any other suitable manner by which the an angle between the two arms 110, 120 is reduced to bias the two arms 110, 120 toward each other. In one non-limiting example, the two arms 110, 120 may be pivotable and fixable (e.g., lockable in the closed position) relative to each other as described in U.S. Pat. No. 9,795,390, the entire disclosure of which is incorporated by reference herein.

When the clip 800 is closed, the two arms 110, 120 are biased toward each other, such that the distal ends 810*a*, 820*a*, respectively, thereof are in close proximity with each other. When the clip 800 is open, the two arms 810, 820 are biased away from each other, such that the distal ends 810*a*, 820*a*, respectively, thereof are spaced apart to form an opening therebetween. An angle between the two arms 810, 820 may change, for example, between 0 and 180 degrees (e.g., between 115 and 155 degrees) when moved between the open and closed positions. As shown in FIG. 8, the two arms 810, 820 are pivoted apart by approximately 120 degrees. Depending on the configuration of the arms 810, 820, the distal ends 810*a*, 820*a*, the mid-segments 810*c*, 820*c*, and the end effector 830, the first distal end 810*a* of the first arm 810 may be in contact with the second distal end 820*a* of the second arm 820 or the end effector 830 when the clip 800 is closed (e.g., when being inserted through the endoscope and/or after clamping the tissue therein).

Each of the two arms 810, 820 may be formed of any of the materials described above with reference to the arms

110, 120, and may be formed by any of the operations described above with reference to the arms 110, 120.

The end effector 830 includes a helical portion 832 and is movable axially and/or rotationally relative to the arms 810, 820. Accordingly, the end effector may include an actuation portion (not shown) coupled with the helical portion 832 that directs the helical portion to move relative to the arms 810, 820. For example, the actuation portion may extend from the helical portion 832 and be coupled to an actuator that, upon manipulation by a clinician, causes the actuation portion to move the helical portion 832 axially and/or rotationally relative to the arms 810, 820. The end effector 830 is configured to pierce and be inserted into the tissue through axial and/or rotational motion generally about a longitudinal axis 830a of the endoscope, which may be generally perpendicular to a pivot axis about which the two arms 810, 820 are moved between the open and closed positions). The helical portion 832 is shaped as a helix and includes a distal end 832a, and one or more turns 832c extending therebetween (e.g., four of the turns 832c, as shown). The distal end 832a is configured to pierce the tissue and may be sharpened or otherwise pointed. The distal end 832a may further include a barb (not shown) to facilitate retention of the tissue on the distal end 832a, for example, as the distal end 832a first pierces the tissue (see also FIGS. 9A and 9B). The end effector 830 may be formed from any materials and by any methods described herein with reference to the end effector 130.

The helical portion 832 of the end effector 830 may be configured according to various characteristics to facilitate piercing and retention of the tissue thereon, such characteristics including number of turns 832c, helical dimension HD, wire dimension (not labeled), and/or pitch or axial gap AG between turns. Such characteristics are the same as those described with reference to the helical portion 132, with the exception being the axial distance AD. In contrast to the helical portion 132, the helical portion 832 does not have a fixed axial distance AD because the helical portion 832 is movable axially relative to the arms 810, 820.

One or more of the arms 810, 820 may include teeth or other serrations (not shown) along the mid-segments 810c, 820c, thereof. Though the teeth are not shown in FIG. 8, they are like the teeth 116, 126 described with reference to FIG. 1. Accordingly, the description of the teeth 116, 126 applies to the teeth that may be implemented as part of the clip 800.

Additionally, and with reference to FIG. 4, the endoscopic system 400 may include the clip 800 instead of the clip 100. The handheld control device 440, by manipulating the operational wire 450 (e.g., by pushing, pulling, and/or rotation) relative to the endoscope 430, may move the clip 800 relative to the endoscope 430 (e.g., by moving the clip axially and/or rotationally relative to the endoscope 430). Manipulating the operational wire 450 may also rotate the clip 800, open and close the clip 800, and lock the clip 800 in the closed position. For example, the clip 800 may be further configured to open, close, and fix into the closed position as described in U.S. Pat. No. 9,795,390, the entire disclosure of which is incorporated by reference herein. In addition, manipulating the operation wire 450 or an additional actuator (not shown) may cause the helical portion to extend and/or retract axially relative to the arms 810, 820 and to rotate relative to the arms 810, 820.

FIGS. 9A and 9B illustrate operation of the endoscopic gastrointestinal clip 800 of FIG. 8 relative to the endoscope 430. FIG. 9A shows the clip 800 in a first stage of tissue engagement, and FIG. 9B shows the clip 800 in a second stage of tissue engagement. In the first stage of tissue engagement, the helical portion 832 has engaged tissue 950 by extending axially relative to the arms 810, 820, engaging the tissue 950 with the distal end 832a, and retracting axially relative to the arms 810, 820. As shown in FIG. 9A, a first portion of the helical portion 832 is located within a clip housing 960. In the second stage of tissue engagement, the helical portion 832 is retracted further into the clip housing 960 as compared to the first stage of tissue engagement such that a second portion of the helical portion 832 is located within the clip housing 960, and the second portion is longer than the first portion.

Furthermore, in the first stage of tissue engagement the arms 810, 820 are located apart from each other at a first angular orientation (for example, approximately 120 degrees). In the second stage of engagement the arms 810, 820 are located apart from each other at a second angular orientation that is smaller than the first angular orientation (for example, approximately 90 degrees).

In some implementations, movement of the helical portion 832 and the arms 810, 820 is coupled. For example, as the helical portion 832 moves axially away from the endoscope 430 the angle between the arms 810, 820 increases and as the helical portion 832 moves axially toward the endoscope 430 the angle between the arms 810, 820 decreases. Axial movement of the helical portion 832 may occur with or without rotation of the helical portion 832. For example, the helical portion 832 may move axially toward the tissue 950 without rotating, and the angle between the arms 810, 820 may increase as the helical portion 832 moves axially toward the tissue without rotating. In some embodiments, as the helical portion 832 is rotated to engage the tissue 950, the angle between the arms 810, 820 may continue to increase. The angle between the arms 810, 820 may also remain unchanged as the helical portion 832 rotates.

In some implementations, movement of the helical portion 832 and the arms 810, 820 is uncoupled. For example, the handheld control device 440 may include separate controls for the helical portion 832 and the arms 810, 820 such that movement of the helical portion 832 does not affect movement or positioning of the arms 810, 820.

Figures 10A, 10B:
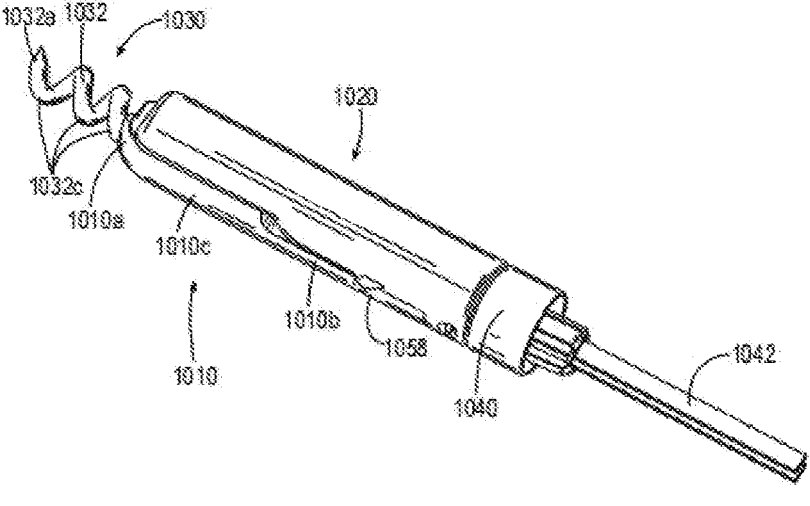
FIGS. 10A-10D are isometric views of another embodiment of an endoscopic gastrointestinal clip in various stages of operation.
Figures 10C, 10D:
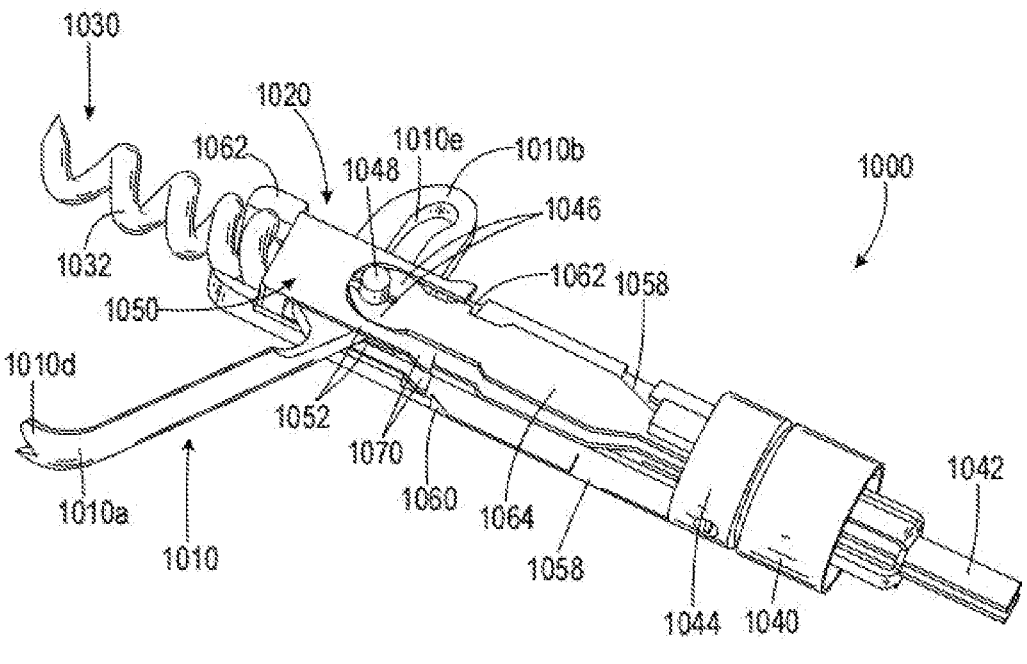

Referring to FIGS. 10A-10D, isometric views of another embodiment of an endoscopic gastrointestinal clip 1000 is shown in various stages of operation. The clip 1000 is configured to be used in endoscopic gastrointestinal procedures to provide closure to large defects in gastrointestinal tissue. The clip 1000 generally includes an arm 1010, a housing 1020, and an end effector 1030. FIG. 10A shows the clip 1000 with the housing 1020 covering the internal components. FIGS. 10B-10D show the clip 1000 with a portion of the housing 1020 removed to show the internal components therein. Unless otherwise described herein, the materials and assembly methods used for the clip 1000 may include any of the materials or assembly methods described with reference to the clip 100 and/or the clip 800.

The end effector 1030 is fixedly coupled to the housing 1020 and extends distally past the distal end 1060 thereof. The end effector 1030 is configured to pierce into and retain therein the tissue of the patient. More particularly, the end effector 1030 is configured to pierce and be inserted into the tissue through rotational motion generally about a longitudinal axis of the housing 1020. As shown and described below, in one embodiment, the end effector 1030 includes a helical portion 1032. The helical portion 1032 is shaped as a helix and includes a distal end 1032a, a proximal end 1032b, and one or more turns 1032c extending therebetween (e.g., four of the turns 132c, as shown). The distal end 1032a is configured to pierce the tissue and may be sharpened or otherwise pointed. The distal end 1032a may further include a barb (not shown) to facilitate retention of the tissue on the distal end 1032a, for example, as the distal end 1032a first pierces the tissue.

The arm 1010 is pivotally coupled to the housing and is longitudinally (e.g., axially) movable relative to the housing 1020 between a closed position (shown in FIGS. 10A and 10D) and an open position (shown in FIGS. 10B and 10C). The arm 1010 is elongated and includes a distal end 1010a, a proximal end 1010b, and a mid-segment 1010c extending between the distal end 1010a and the proximal end 1010b. The distal end 1010a may include a retaining feature 1010d that is configured to hold tissue. For example, the retaining feature 1010d may include a barb. The proximal end 1010b defines a cam surface 1010e that extends through the proximal end 1010b and is sized to receive a pin 1048. The pin 1048 is secured by retention arms 1046 that extend from a support arm 1064 such that the pin 1048 does not move relative to the retention arms 1046 in the longitudinal direction. In some implementations, two support arms 1064 are used, and each of the support arms 1064 is coupled on opposing sides of an actuation arm 1042. In some embodiments, the support arms 1064 and the actuation arm 1042 are a unitary body. The support arms 1064 and the actuation arm 1042 may also be separate components that are joined together. In instances where two support arms 1064 are implemented, the support arms 1064 extend over opposing external surfaces of the proximal end 1010b such that the pin 1048 is secured to retention arms 1046 on either side of the proximal end 1010b. Arranged as described, the arm 1010 is movably fixed to the pin 1048 and moves according to the interaction between the pin 1048 and the cam surface 1010e.

The actuation arm 1042 may be coupled to an actuator located on the handheld control device 440 and is configured to move in the longitudinal (e.g., axial) direction. For example, the actuation arm 1042 can move toward and away from the end effector 1030 based on a corresponding action of the actuator located on the handheld control device 440. The motion of the actuation arm 1042 toward and away from the end effector 1030 causes a corresponding motion of the support arms 1064, the retention arms 1046, and the pin 1048. Accordingly, when the actuation arm moves toward the end effector 1030 the support arms 1064, the retention arms 1046, and the pin 1048 also move toward the end effector 1030. Conversely, when the actuation arm moves away from the end effector 1030 the support arms 1064, the retention arms 1046, and the pin 1048 also move away from the end effector 1030.

The proximal end 1010b is also at least partially located within a shuttle 1050 that is configured to slide longitudinally within the housing 1020. The shuttle 1050 includes posts 1052 that extend from a body of the shuttle 1050 in a direction away from the end effector 1030. Each of the posts 1052 terminates in a tab 1070, where a width of the tabs 1070 is greater than a width of the posts 1052. The shuttle 1050 is constructed from a material that can withstand some deformation and return to its original shape. For example, each of the posts 1052 can deform in response to a force applied in a direction approximately perpendicular to the longitudinal axis of the clip 1000 and then return to their original shapes and orientation when the force is removed. As shown, the shuttle 1050 includes four posts 1052, with two of the posts 1052 positioned adjacent to one outer surface of the proximal portion 1010b and two of the posts 1052 positioned adjacent to the opposite outer surface of the proximal portion 1010b. Each pair of the posts 1052 positioned on opposite sides of the proximal portion 1010b also defines a space therebetween that is sized and configured to receive the retention arms 1046.

Each of the tabs 1070 is sized to interface with a slot defined by the housing 1020. As shown, the housing 1020 defines proximal slots 1058 and distal slots 1062. In some implementations the proximal slots 1058 and the distal slots 1062 extend through the housing 1020 such that the proximal slots 1058 and the distal slots 1062 are visible to the clinician. The proximal slots 1058 and the distal slots 1062 may also extend only partially through the housing 1020 such that the proximal slots 1058 and the distal slots 1062 are not visible to the clinician. Each of the tabs 1070 includes a ramp 1072 located on a distal portion of the tabs 1070 that interfaces with the corresponding slot to allow for movement of the shuttle 1050 in the distal direction. Each of the tabs 1070 also includes a flat portion 1074 that interfaces with the corresponding slot to prevent movement of the shuttle 1050 in the proximal direction. Movement of shuttle 1050 will be further described below.

The housing 1020 includes a first surface 1054 configured to support the shuttle 1050 as the shuttle 1050 moves within the housing 1020. In some implementations, the first surface 1054 may include a lubricious coating that facilitates movement of the shuttle 1050 within the housing 1020. The first surface 1054 also defines a second surface 1056 that is recessed below the first surface 1054 and is sized to support and secure the pin 1048 as the pin 1048 moves within the housing 1020. The housing 1020 is coupled to a distal coupling portion 1044, and the distal coupling portion is releasably connected to a proximal coupling portion 1040. In various implementations, the distal coupling portion 1044 can be removed from the proximal coupling portion 1040 to leave a portion of the clip 1000 in the patient.

In operation, the clip 1000 is provided to a clinician in a closed configuration as shown in FIG. 10A (e.g., the distal end 1010a is positioned adjacent to a proximal end of the helical portion 1032). Though not shown in FIG. 10A, the actuation arm 1042 is retracted in the proximal direction (e.g., closer to the distal coupling portion 1044), thereby causing the pin 1048 to be retracted in the proximal direction as well. When the pin 1048 is in the retracted position, the retention arms 1046 are longitudinally spaced apart from (e.g., not in contact with) the shuttle 1050. In the retracted position, the pin 1048 causes the arm 1010 to be in the closed position. The clinician may insert the clip 1000 through an endoscope (e.g., the endoscope 430) and rotate the clip 1000 to cause the distal end 1032a to engage tissue.

To open the clip 1000 the clinician actuates the actuation arm 1042 to move the actuation arm 1042 in the distal direction. This movement causes the retention arms 1046 to move the pin 1048 in the distal direction until the retention arms 1046 contacts the shuttle 1050. As the pin 1048 moves in the distal direction, the movement of the pin 1048 within the cam surface 1010e causes the proximal end 1010b to move, thereby causing the distal end 1010a to pivot away from the housing 1020 and the helical portion 1032, as shown in FIG. 10B, to position the clip 1000 in an open configuration.

As the clinician continues to attempt to move the actuation arm 1042 in the distal direction, the tabs 1070 contact the proximal slots 1058 at the ramps 1072. As the force applied to the actuation arm 1042 increases, the proximal slots 1058 apply forces to the ramps 1072, which causes the posts 1052 to deform inward (e.g., toward the pin 1048) and allows the ramps 1072 to move along the proximal slots 1058 until the tabs 1070 are within the housing 1020. As the actuation arm 1042 continues to move in the distal direction, which causes the shuttle and the arm 1010 to move in the distal direction, the distal end 1010a and the retaining feature 1010d may contact additional tissue and draw the additional tissue distally.

When the tabs 1070 reach the distal slots 1062, the deformation force applied to the posts 1052 is released, allowing the posts 1052 to return to their original position and orientation, which in turn causes the tabs 1070 to interface with the distal slots 1062 to secure the shuttle 1050 in a distal position, as shown in FIG. 10C. Once secured in the distal position, the interaction between the flat portions 1074 and the distal slots 1062 prevents the shuttle 1050 from being moved proximally.

To close the clip 1000 and close or correct the defect, the clinician moves the actuation arm 1042 in the proximal direction, which causes the pin 1048 to move in the proximal direction. The movement of the pin 1048 causes the proximal end 1010b to move as the cam surface 1010e contacts the pin 1048. The movement of the proximal end 1010b causes the retaining feature 1010d and the distal end 1010a to move toward the distal end 1032a of the helical portion 1032, thereby bringing tissue engaged by the retaining feature 1010d in contact with tissue engaged by the helical portion 1032.

The features described with reference to FIGS. 10A-10D can be implemented with any of the embodiments described herein. For example, the clip 100 may include features like the ones described with reference to FIGS. 10A-10D that cause the arms 110, 120 to open and close. In addition, the clip 800 may include features like the ones described with reference to FIGS. 10A-10D that cause the arms 810, 820 to open and close.

Figure 11:
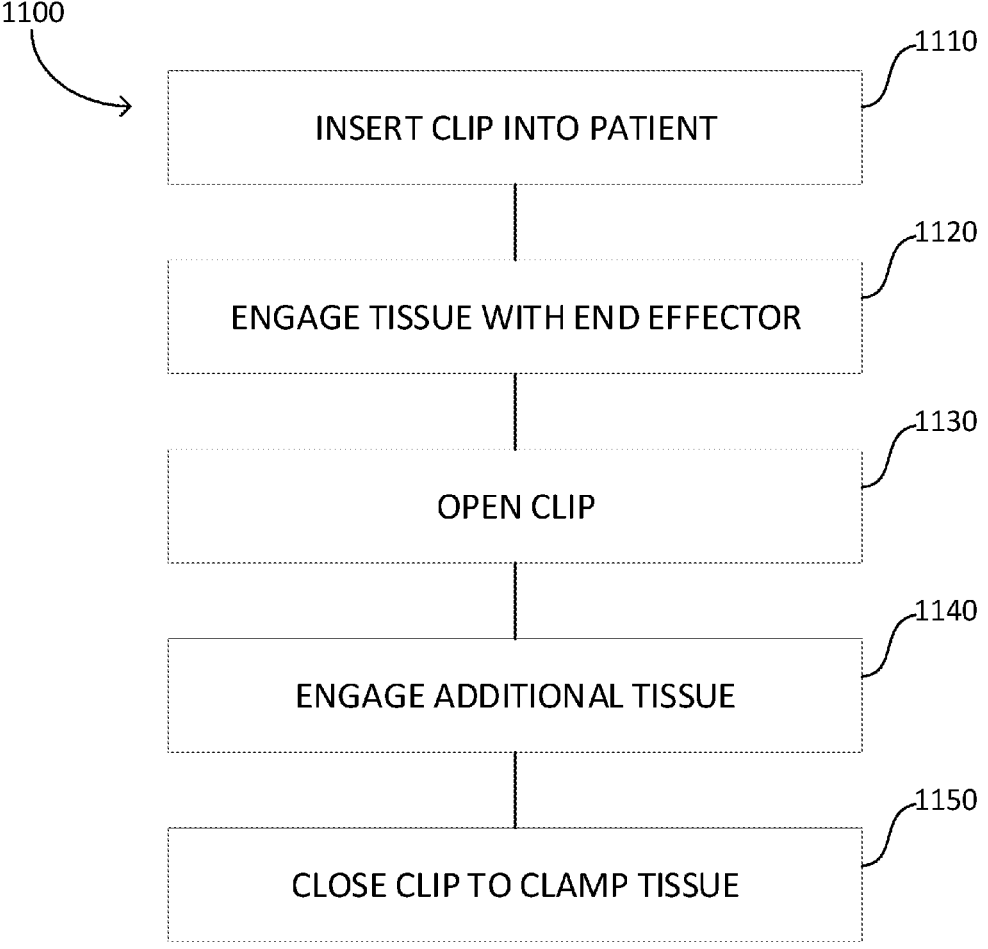
FIG. 11 is a flowchart of a method for closing a gastrointestinal defect with the endoscopic gastrointestinal clip of FIG. 1.

FIG. 11 is a flowchart of a method 1100 for closing a gastrointestinal defect with the clip 100 of FIG. 1 and the clip 1000 of FIGS. 10A-10D. For example, during an endoscopic procedure the clinician may desire to close a defect in tissue by bringing two tissue portions together. The clinician may introduce an endoscope (e.g., the endoscope 430) into the desired location in the patient. In some implementations, the endoscope 430 is steerable such that a distal end of the endoscope 430 can be repositioned in the body of the patient. At operation 1110, a clip is inserted into the patient. In some embodiments, the clip 100 is inserted to the desired location through a lumen in the endoscope 430. In some embodiments, the clip 1000 is inserted to the desired location through a lumen in the endoscope 430.

At operation 1120, tissue is engaged with an end effector. For example, to engage the desired tissue the clinician may move the clip 100 (e.g., move the clip 100 in an axial direction relative to the endoscope 430) until the distal end 132a of the helical portion 132 contacts the desired tissue. Upon contact, the clinician may rotate the clip 100 to cause the distal end 132a to engage (e.g., pierce) the tissue. The clinician may rotate the clip 100 multiple times to cause the helical portion 132 to move deeper into the tissue to ensure a secure connection between the helical portion 132 and the tissue.

As an additional example, to engage the desired tissue the clinician may move the clip 1000 until the distal end 1032a of the helical portion 1032 contacts the desired tissue. Upon contact, the clinician may rotate the clip 1000 to cause the distal end 1032a to engage (e.g., pierce) the tissue. The clinician may rotate the clip 1000 multiple times to cause the helical portion 1032 to move deeper into the tissue to ensure a secure connection between the helical portion 1032 and the tissue.

At operation 1130, the clip is opened. For example, the clinician opens the clip 100 by separating the arms 110, 120. This action may cause the tissue engaged by the helical portion 132 to move from its original location. As an additional example, the clinician opens the clip 1000 as described above with reference to FIGS. 10A-10D. The clip 100 may be opened in the same manner as the clip 1000 (e.g., by using components like the ones described with reference to the clip 1000).

At operation 1140, additional tissue is engaged. For example, the clinician may move the clip to draw the engaged tissue across the defect to close or correct the defect. The movement of the tissue may be caused by a corresponding movement of the clip 100 (e.g., axial or rotational movement of the clip 100), by a corresponding movement of the endoscope 430 (e.g., movement of the distal end of the endoscope 430), or a combination thereof. Such movement of the clip may also cause unengaged tissue (e.g., tissue that is not engaged by the helical portion 132) to be located between the arms 110, 120.

As an additional example, the clinician may move the arm 1010 distally as described above to draw additional tissue toward the distal end of the clip 1000 and the helical portion 1032.

At operation 1150, the clip is closed to clamp the tissue. For example, the clinician causes the arms 110, 120 to close via an actuator located on the handheld control device 440, thereby causing the tissue positioned between the arms 110, 120 to be compressed and held between the arms 110, 120. The tissue positioned between the arms 110, 120 may include a portion of the engaged tissue (e.g., the tissue connected to the helical portion 132) and the unengaged tissue such that the engaged tissue and the unengaged tissue are held together by the arms 110, 120 when the arms 110, 120 are closed. In embodiments that include the teeth 116, 126, the teeth 116, 126 may also contact the engaged tissue, the unengaged tissue, or both the engaged tissue and the unengaged tissue to hold the tissue. Holding the tissue together causes the defect to be corrected and/or closed.

As an additional example, the clinician causes the arm 1010 to close as described above, thereby causing the tissue engaged by the helical portion 1032 and the tissue engaged by the retaining feature 1010d to be compressed and held together. Compressing and holding the tissue together causes the defect to be corrected and/or closed.

In some implementations, the clip 100 and the clip 1000 can be detached (e.g., by detaching the distal coupling portion 1044 from the proximal coupling portion 1040) and remain in the body to hold the tissue together to facilitate defect correction and/or closure after the procedure is complete.

Figure 12:
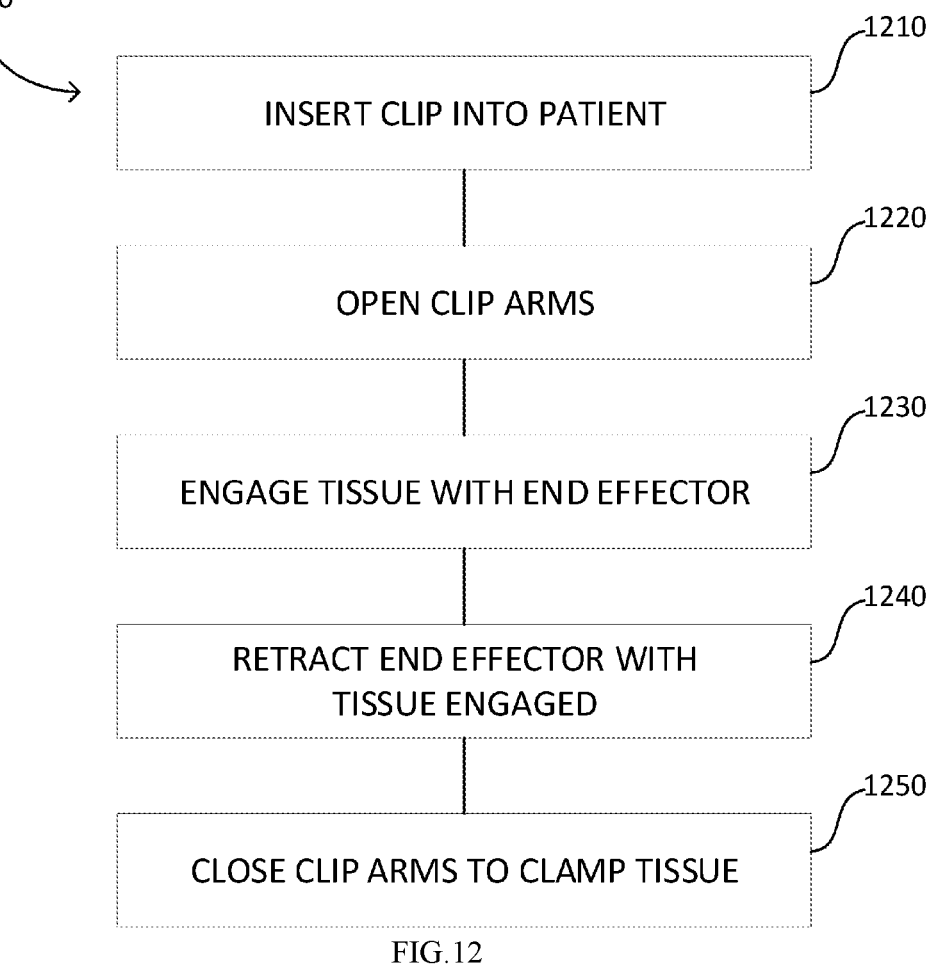
FIG. 12 is a flowchart of a method for closing a gastrointestinal defect with the endoscopic gastrointestinal clip of FIG. 8.

FIG. 12 is a flowchart of a method for closing a gastrointestinal defect with the endoscopic gastrointestinal clip 800 of FIG. 8. For example, and with reference to FIGS. 8-9, during an endoscopic procedure the clinician may desire to close a defect in tissue by bringing two tissue portions together. The clinician may introduce an endoscope (e.g., the endoscope 430) into the desired location in the patient. In some implementations, the endoscope 430 is steerable such that a distal end of the endoscope 430 can be repositioned in the body of the patient. At operation 1210, a clip is inserted into the patient. In some embodiments, the clip 800 is inserted to the desired location through a lumen in the endoscope 430. When the clip 800 is inserted to the desired location, the helical portion 832 is prevented from contacting tissue. In some embodiments, the helical portion 832 is prevented from contacting tissue by the arms 810, 820, which cover the helical portion 832 when the arms 810, 820 are in the closed position. In some implementations, the helical portion 832 is prevented from contacting tissue because the helical portion 832 is in a retracted position where the distal end 832*a* is located within the clip housing 960. In some embodiments, the helical portion 832 is prevented from contacting tissue because the arms 810, 820 are in the closed position and the helical portion 832 is in the retracted position.

At operation 1220, the clip arms are opened. For example, the clinician may operate an actuator coupled to the hand-held control device 440 to cause the arms 810, 820 to open, thereby increasing the angle between the arms 810, 820.

At operation 1230, tissue is engaged with an end effector. For example, and with reference to FIG. 9A, the helical portion 832 is extended toward the target tissue (e.g., the tissue 950) by a combination of axial and/or rotational movement imparted to the helical portion by the handheld control device 440. In some instances, the clinician may extend the helical portion 832 axially until the distal end 832*a* contacts the target tissue, and then the clinician may rotate the helical portion 832 to cause the distal end 832*a* to engage (e.g., pierce) the tissue 950. The clinician may continue to rotate the helical portion 832 until multiple coils of the helical portion 832 are engaged with the tissue 950.

At operation 1240, the end effector is retracted with the tissue engaged. For example, and with reference to FIG. 9B, the clinician may retract the helical portion 832 toward the endoscope 430 (e.g., by moving the helical portion 832 axially without imparting a rotation) such that the tissue 950 is drawn toward the endoscope 430. As the tissue 950 (e.g., the engaged tissue) moves toward the endoscope 430, additional tissue connected to the tissue 950 (e.g., unengaged tissue) is drawn toward the endoscope such that the additional tissue is positioned between the arms 810, 820.

At operation 1250, the clip arms are closed to clamp the tissue. For example, the clinician may cause the arms 810, 820 to close (e.g., by manipulating an actuator positioned on the handheld device 440) such that the additional tissue is held between the distal ends 810*a*, 820*a*. The distal ends 810*a*, 820*a* may include features to facilitate closure and/or holding the tissue. For example, the distal ends 810*a*, 820*a* may include teeth and/or other protrusions or serrations and corresponding recesses that cooperate (e.g., similarly to the teeth 116, 126) to capture and hold the tissue. In addition, the tissue 950 remains engaged by the helical portion 832 when the arms 810, 820 are closed such that there are three points of contact (e.g., the distal ends 810*a*, 820*a* and the helical portion 832) between the tissue and the clip 800 to facilitate defect closure and/or correction.

In some implementations, the clip 800 can be detached and remain in the body to hold the tissue together to facilitate defect correction and/or closure after the procedure is complete.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A clip for use in an endoscopic gastrointestinal procedure, the clip comprising:
   a first arm having a first proximal end and a first distal end;
   a second arm having a second proximal end and a second distal end; and
   an end effector fixedly to the second arm and extending from the second arm distally relative to the second distal end;
   wherein the first arm and the second arm are pivotable relative to each other between an open position and a closed position in which tissue is clampable between the first arm and the second arm; and
   wherein the end effector is so configured that: with the clip remaining closed, the end effector is inserted into the tissue by rotating the clip about a longitudinal axis of an endoscope.

2. The clip according to claim 1, wherein the first axis that is generally perpendicular to a second axis about which one or more of the first arm and the second arm are pivotable between the open position and the closed position.

3. The clip according to claim 1, wherein the end effector is configured to be inserted into the tissue by at least one rotation thereof about the first axis.

4. The clip according to claim 1, wherein the end effector includes a helical portion having one or more turns that circumscribe the first axis.

5. The clip according to claim 4, wherein when in the closed position, at least one of the one or more turns extends distally beyond the first distal end of the first arm.

6. The clip according to claim 4, wherein the helical portion includes a distal end that is sharpened.

7. The clip according to claim 6, wherein the distal end of the helical portion includes a barb.

8. The clip according to claim 4, wherein when in the closed position, a proximal portion of the helical portion extends at least part of one turn proximally of the first distal end of the first arm.

9. The clip according to claim 8, wherein the first distal end of the first arm defines a recess that receives the proximal portion of the helical portion therein.

10. The clip according to claim 1, wherein the first arm includes a first mid-segment that extends between the first distal end and the first proximal end, the second arm includes a second mid-segment that extends between the second distal end and the second proximal end, and one or both of the first mid-segment and the second mid-segment includes teeth that engage and retain the tissue when clamped between the first arm and the second arm.

11. The clip according to claim 10, wherein both of the first mid-segment and the second mid-segment include the teeth that intermesh when in the closed position.

* * * * *